(12) United States Patent
Green et al.

(10) Patent No.: US 8,409,806 B2
(45) Date of Patent: Apr. 2, 2013

(54) ALLELIC LADDER LOCI

(75) Inventors: Robert Green, Cupertino, CA (US);
Julio Mulero, Sunnyvale, CA (US);
Lori Hennessy, San Mateo, CA (US);
Robert Lagace, Oakland, CA (US);
Chien-Wei Chang, Belmont, CA (US)

(73) Assignee: Life Technologies Corporation, Carlsbad, CA (US)

(*) Notice: Subject to any disclaimer, the term of this patent is extended or adjusted under 35 U.S.C. 154(b) by 120 days.

(21) Appl. No.: 12/954,551

(22) Filed: Nov. 24, 2010

(65) Prior Publication Data

US 2011/0171654 A1 Jul. 14, 2011

Related U.S. Application Data

(60) Provisional application No. 61/264,455, filed on Nov. 25, 2009.

(51) Int. Cl.
*C12Q 1/68* (2006.01)
*C12P 19/34* (2006.01)

(52) U.S. Cl. ...................... 435/6.12; 435/91.2
(58) Field of Classification Search ................. 435/6.12, 435/91.2
See application file for complete search history.

(56) References Cited

U.S. PATENT DOCUMENTS

| | | | |
|---|---|---|---|
| 5,783,406 A | 7/1998 | Schumm et al. | |
| 5,994,064 A | 11/1999 | Staub et al. | |
| 6,156,512 A | 12/2000 | Schumm et al. | |
| 7,087,380 B2 | 8/2006 | Griffiths et al. | |
| 2009/0004662 A1* | 1/2009 | Mulero et al. | 435/6 |
| 2009/0142764 A1 | 6/2009 | Hennessy et al. | |
| 2011/0171654 A1* | 7/2011 | Green et al. | 435/6.12 |

FOREIGN PATENT DOCUMENTS

WO WO-2011/066467 A2 6/2011

OTHER PUBLICATIONS

Promega Technical Manual "PowerPlex ESX 16_UM", Aug. 2009.
Chung, Ukhee et al., "Population data of nine miniSTR loci in Koreans", Forensic Science International, 168, 2007, e51-e53.
Coble, M. D. et al., "Characterization of new MiniSTR loci to aid analysis of degraded DNA", Journal of Forensic Sciences, vol. 50(1), Jan. 2005, 43-53 (pp. 1-11 as presented).
PCT/US2010/058111, "International Search Report and Written Opinion", mailed Sep. 7, 2011.

* cited by examiner

*Primary Examiner* — Kenneth R. Horlick
*Assistant Examiner* — Joyce Tung

(57) ABSTRACT

Disclosed are rare short tandem repeat (STR) alleles within the D10S1248 and D12S391 loci in humans. Provided are representative allelic ladders for each locus, methods and assays using these alleles and kits containing allelic ladders comprising these alleles for accurate genotyping and identification of a wide range of individuals.

24 Claims, 1 Drawing Sheet

D12S391 allele-14
5'
AGCGGCCGCGAATTCGCCCTTTCCTGGAGCTGCGACACATTCTTCTGCCCTTGGAAGTCAGAGCTCCAGGCTCTCCTGTCTTTGTACTCTGGGACTTAT
ACCAGGGGCACTCCAGGTTCTCAGGCCTTCCACCTGGGATGGATAATTACACCATCAGTTTCCCTGGTTTTTTGGCTTTTAGACCTGGACTGAGCCATG
CTCCTAGTGTCCCTGGGTCTCCAGCTTGCAGATGGACTGTCATGAGATTTTTCAGCCTCCATATCACTTGAGCTAATTCCTCTAATAAATCCCCTCTCA
TCTGTCTGTCTGTCTGTCTGTCTGTCTATCTATCTATCTATCTATCTATCTATCTACCTATGCATCCATTGATCCTGTTGATTCTTTCTCTCTGGAGAA
GCCTTACTAATACAGTCTCTTTTTTCATCTTCCCTGATATCATTCTCTTTTCTTCCTTCACCAGAAGGGCGAATTCGTTTAAACCTGCAGGACTAGTCC
CTTTAGTGAGGGTTAATTCTGAGCTTGGCGTAATCATGGTC 3' (SEQ ID NO:6)

D12S391 allele-27
5'
AGCGGCCGCGAATTCGCCCTTTCCTGGAGCTGCGACACATTCTTCTGCCCTTGGAAGTCAGAGCTCCAGGCTCTCCTGTCTTTGTACTCTGGGACTTAT
ACCAGGGGCACTCCAGGTTCTCAGGCCTTCCACCTGGGATGGATAATTACACCATCAGTTTCCCTGGTTTTTAACAGGATCAATGGA**TGCATAGGTAGA
TAGATAGATAGATAGATAGATAGATAGATAGATAGATAGATAGATAGATAGATAGATAGATAGATAGACAGACAGACAGACAGACAGACAGACAG
ACAGAT**GAGAGGGGATTTATTAGAGGAATTAGCTCAAGTGATATGGAGGCTGAGAAATCTCATGACAGTCCATCTGCAAGCTGGAGACCCAGGGACACT
AGGAGCATGGCTCAGTCCAGGTCTAAAAGCCAGATTCTTTCTCTCTGGAGAAGCCTTACTAATACAGTCTCTTTTTTCATCTTCCCTGATATCATTCTC
TTTTCTTCCTTCACCAGAAGGGCGAATTCGTTTAAACCTGCAGGACTAGTCCCTTTAGTGAGGGTTAATTCTGAGCTTGGCGTAATCATGGTC 3' (SEQ
ID NO:7)

SEQUENCE LISTING

```
<160> NUMBER OF SEQ ID NOS: 14

<210> SEQ ID NO 1
<211> LENGTH: 21
<212> TYPE: DNA
<213> ORGANISM: Homo sapiens

<400> SEQUENCE: 1
atcatcatca tcaacatcat c                                            21

<210> SEQ ID NO 2
<211> LENGTH: 20
<212> TYPE: DNA
<213> ORGANISM: Homo sapiens

<400> SEQUENCE: 2
gatagataga tacatagata                                              20

<210> SEQ ID NO 3
<211> LENGTH: 15
<212> TYPE: DNA
<213> ORGANISM: Homo sapiens

<400> SEQUENCE: 3
attgcattgc attgc                                                   15

<210> SEQ ID NO 4
<211> LENGTH: 20
<212> TYPE: DNA
<213> ORGANISM: Homo sapiens

<400> SEQUENCE: 4
atcgatcgaa cgatcgatcg                                              20

<210> SEQ ID NO 5
<211> LENGTH: 28
<212> TYPE: DNA
<213> ORGANISM: Homo sapiens
```

<400> SEQUENCE: 5

```
atccatcgat ccatcgatcg atccatcc                                         28
```

<210> SEQ ID NO 6
<211> LENGTH: 536
<212> TYPE: DNA
<213> ORGANISM: Homo sapiens

<400> SEQUENCE: 6

```
agcggccgcg aattcgccct tcctggagc tgcgacacat tcttctgccc ttggaagtca      60
gagctccagg ctctcctgtc tttgtactct gggacttata ccaggggcac tccaggttct    120
caggccttcc acctgggatg gataattaca ccatcagttt ccctggtttt ttggctttta    180
gacctggact gagccatgct cctagtgtcc ctgggtctcc agcttgcaga tggactgtca    240
tgagattttt cagcctccat atcacttgag ctaattcctc taataaatcc cctctcatct    300
gtctgtctgt ctgtctgtct gtctatctat ctatctatct atctatctat ctacctatgc    360
atccattgat cctgttgatt cttttctctct ggagaagcct tactaataca gtctctttt     420
tcatcttccc tgatatcatt ctcttttctt ccttcaccag aagggcgaat tcgtttaaac    480
ctgcaggact agtccctta gtgagggtta attctgagct tggcgtaatc atggtc         536
```

<210> SEQ ID NO 7
<211> LENGTH: 588
<212> TYPE: DNA
<213> ORGANISM: Homo sapiens

<400> SEQUENCE: 7

```
agcggccgcg aattcgccct tcctggagc tgcgacacat tcttctgccc ttggaagtca      60
gagctccagg ctctcctgtc tttgtactct gggacttata ccaggggcac tccaggttct    120
caggccttcc acctgggatg gataattaca ccatcagttt ccctggtttt taacaggatc    180
aatggatgca taggtagata gatagataga tagatagata gatagataga tagatagata    240
gatagataga tagatagata gatagataga cagacagaca gacagacaga cagacagaca    300
gatgagaggg gatttattag aggaattagc tcaagtgata tggaggctga gaaatctcat    360
gacagtccat ctgcaagctg gagacccagg gacactagga gcatggctca gtccaggtct    420
aaaagccaga ttctttctct ctggagaagc cttactaata cagtctcttt tttcatcttc    480
cctgatatca ttctcttttc ttccttcacc agaagggcga attcgtttaa acctgcagga    540
ctagtccctt tagtgagggt taattctgag cttggcgtaa tcatggtc                 588
```

<210> SEQ ID NO 8
<211> LENGTH: 36
<212> TYPE: DNA
<213> ORGANISM: Homo sapiens

<400> SEQUENCE: 8

```
aatgaatgaa tgaatgaatg aatgaatgaa tgaatg                               36
```

<210> SEQ ID NO 9
<211> LENGTH: 39
<212> TYPE: DNA
<213> ORGANISM: Homo sapiens

<400> SEQUENCE: 9

```
aatgaatgaa tgaatgaatg aatgatgaat gaatgaatg                            39
```

<210> SEQ ID NO 10

-continued

```
<211> LENGTH: 28
<212> TYPE: DNA
<213> ORGANISM: Homo sapiens

<400> SEQUENCE: 10
ggaaggaagg aaggaaggaa ggaaggaa                                          28

<210> SEQ ID NO 11
<211> LENGTH: 52
<212> TYPE: DNA
<213> ORGANISM: Homo sapiens

<400> SEQUENCE: 11
agatagatag atagatagat agatagacag acagacagac agacagacag at              52

<210> SEQ ID NO 12
<211> LENGTH: 76
<212> TYPE: DNA
<213> ORGANISM: Homo sapiens
<220> FEATURE:
<221> NAME/KEY: misc_feature
<222> LOCATION: (1)..(76)
<223> OTHER INFORMATION: This region may encompass 8 to 19 repeating
      "ggaa" nucleotides

<400> SEQUENCE: 12
ggaaggaagg aaggaaggaa ggaaggaagg aaggaaggaa ggaaggaagg aaggaaggaa      60
ggaaggaagg aaggaa                                                      76

<210> SEQ ID NO 13
<211> LENGTH: 32
<212> TYPE: DNA
<213> ORGANISM: Homo sapiens

<400> SEQUENCE: 13
ggaaggaagg aaggaaggaa ggaaggaagg aa                                    32

<210> SEQ ID NO 14
<211> LENGTH: 112
<212> TYPE: DNA
<213> ORGANISM: Homo sapiens
<220> FEATURE:
<221> NAME/KEY: misc_feature
<222> LOCATION: (1)..(68)
<223> OTHER INFORMATION: This region may encompass 8 to 17 repeating
      "agat" nucleotides
<220> FEATURE:
<221> NAME/KEY: misc_feature
<222> LOCATION: (69)..(108)
<223> OTHER INFORMATION: This region may encompass 6 or 8 to 10
      repeating "agac" nucleotides
<220> FEATURE:
<221> NAME/KEY: misc_feature
<222> LOCATION: (109)..(112)
<223> OTHER INFORMATION: This region may or may not be present

<400> SEQUENCE: 14
agatagatag atagatagat agatagatag atagatagat agatagatag atagatagat      60
agatagatag acagacagac agacagacag acagacagac agacagacag at             112
```

ALLELIC LADDER LOCI

FIELD

In general, the disclosed invention relates to the identification of novel short tandem repeat (STR) alleles within the D10S1248 and D12S391 loci in humans. The discovery of new alleles provides a more representative allelic ladder for each locus and the ability to accurately genotype a wider range of individuals.

BACKGROUND

The fields of forensics, paternity testing, tissue typing, and personalized medicine routinely use DNA-based techniques for identity determinations, genotyping, phenotypic prediction, and in the prediction and/or prevention of disease. DNA typing involves the analysis of alleles of genomic DNA with characteristics of interest, commonly referred to as "markers." Most typing methods in use today are specifically designed to detect and analyze differences in the length and/or sequence of one or more regions of DNA markers known to appear in at least two different forms in a population. Such length and/or sequence variation is referred to as "polymorphism." Any region (i.e., "locus") of DNA in which such a variation occurs is referred to as a "polymorphic locus."

In recent years, the discovery and development of polymorphic short tandem repeats (STRs) as genetic markers has played an important role in DNA typing. STRs have become the primary means for human identity and forensic DNA testing. The Combined DNA Index System (CODIS) DNA database operated by the Federal Bureau of Investigation stores the DNA profile information of selected individuals. The CODIS profile includes 13 STR markers (13 loci with STR repeats), two additional allelic markers and AMEL, a sex determination allele. The selected DNA profiles can be from many possible sources, e.g., convicted offenders, arrestees, missing or unidentified persons, and missing persons reference DNA (blood relative). Comparison of the DNA profile of an unidentified sample to CODIS DNA profiles has provided potential identification matches or investigative leads of possible perpetrators.

Matching and comparing DNA profiles produced from existing commercial STR assays provides continuity and comparability of the DNA profiles within and between databases and improved STR assays. The use of a size standard, i.e., an allelic ladder, composed of amplified alleles from a locus, permits comparison of STR alleles for the locus between databases, STR assays, laboratories and samples to increase the power of the DNA profiling system.

Thus, identification of rare alleles, which can be highly discriminating, further improves determination of alleles in unidentified samples. Therefore, there exists a need in the art, to improve DNA-based technologies based on the discovery of new STR alleles in human DNA sequences.

SUMMARY OF SOME EMBODIMENTS OF THE INVENTION

In some embodiments, disclosed is an allelic ladder comprising, in combination, an isolated plurality of nucleic acid molecules which are allelic variants of one or more polymorphic short tandem repeat loci, wherein the polymorphic short tandem repeat locus is selected from the group consisting of D10S1248 comprising allele-7 and D12S391 comprising allele-13. Also envisioned are methods of using allelic ladders, assays employing allelic ladders and kits having allelic ladders for the D10S1248 and D12S391 STR markers.

These embodiments and other features of the present teachings will become more apparent from the description herein.

BRIEF DESCRIPTION OF THE DRAWINGS

FIG. 1 illustrates the STR regions for alleles 14 and 27 for the D12S391 locus.

SEQUENCE LISTING

The instant application contains a Sequence Listing which has been submitted in ASCII format via EFS-Web and is hereby incorporated by reference in its entirety. Said ASCII copy, created on Dec. 15, 2010, is named LT0071 US.txt and is 4,286 bytes in size.

DESCRIPTION OF EXEMPLARY EMBODIMENTS

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. For illustration purposes, but not as a limitation, "X and/or Y" can mean "X" or "Y" or "X and Y". The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of". The term "and/or" means one or all of the listed elements or a combination of any two or more of the listed element.

The section headings used herein are for organizational purposes only and are not to be construed as limiting the described subject matter in any way. All literature cited in this specification, including but not limited to, patents, patent applications, articles, books, and treatises are expressly incorporated by reference in their entirety for any purpose. In the event that any of the incorporated literature contradicts any term defined herein, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The practice of the present invention may employ conventional techniques and descriptions of organic chemistry, polymer technology, molecular biology (including recombinant techniques), cell biology, biochemistry, and immunology, which are within the skill of the art. Such conventional techniques include oligonucleotide synthesis, hybridization, extension reaction, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), PCR Primer: A Laboratory Manual, and Molecular Cloning: A Laboratory Manual (all from Cold Spring Harbor Laboratory Press, 1989), Gait, "Oligonucleotide Synthesis: A Practical Approach" 1984, IRL Press, London, Nelson and Cox (2000), Lehninger, Principles of Biochemistry $3^{rd}$ Ed., W. H. Freeman Pub., New York, N.Y. and Berg et al. (2002) Biochemistry, $5^{th}$ Ed., W. H. Freeman Pub., New York, N.Y. all of which are herein incorporated in their entirety by reference for all purposes.

The term "allele" as used herein refers to a genetic variation associated with a gene or a segment of DNA, i.e., one of two or more alternate forms of a DNA sequence occupying the same locus.

The term "locus" as used herein refers to a specific physical position on a chromosome or a nucleic acid molecule. Alleles of a locus are located at identical sites on homologous chromosomes. "Loci" the plural of "locus" as used herein refers to a specific physical position on either the same or a different chromosome as well as either the same or a different specific physical position on the nucleic acid molecule.

The term "allelic ladder" as used herein refers to a nucleic acid size standard that comprises size standards for one or more alleles for a particular STR marker. The allelic ladder serves as a reference standard and nucleic acid size marker for the amplified alleles from the locus. In some embodiments, the allelic ladder can comprise size standards for the alleles of different STRs. In some embodiments, the allelic ladder can be made of DNA. In some embodiments the allelic ladder can be made of non-naturally occurring nucleic acid analogs. The different individual size standards within an allelic ladder can, in some embodiments can be labeled with a detectable label, e.g., a fluorophore. In some embodiments, the allelic ladder components are labeled with the same fluorophore. In some embodiments, the allelic ladder components are labeled with the different fluorophores. The size standards can be selected to work for a specific pair (or pairs) of oligonucleotides primers. For example if a first set of primers for marker X produces a 150 base pair amplicon corresponding to allele 7, the corresponding marker will serve as a size standard for the 150 base amplicons; while a second pair of primers marker X produces a 175 base pair amplicon corresponding to allele 7, the corresponding marker will serve as a size standard for the 175 base amplicons. Thus different size standards for different size amplicons of the same allele are contemplated. The size standard for a given amplicon derived from a given allele may have nucleic acid base sequence that is the same or different than the nucleic acid base sequence of the amplicon or allele from which the amplicon is derived. For allele analysis in electrophoresis systems the size standard can be selected so as to have the same electrophoretic mobility as the amplicon of interest. Alternatively, in some embodiments, the size standard can be selected so as to have the different electrophoretic mobility than the amplicon of interest, given an understanding of the predicable nature of the difference, the identity of the amplicons could be determined. For allele analysis in mass spectroscopy systems the size standard (weight/charge ratio, not electrophoretic mobility) can be selected so as to have the same signal as the amplicon of interest. Alternatively, in some embodiments, the size standard (weight/charge ratio, not electrophoretic mobility) can be selected so as to have the different separation properties than the amplicon of interest, given an understanding of the predicable nature of the difference, the identity of the amplicons could be determined.

The term "allelic variant" as used herein refers to the variation between two or more alleles within a locus. The allelic variant can also be referred to as a polymorphism.

As used herein, the term "base pair motif" refers to the nucleobase sequence configuration including, but not limited to, a repetitive sequence, a sequence with a biological significance, a tandem repeat sequence, and so on.

As used herein, the term "comparing" broadly refers to differences between two or more nucleic acid sequences. The similarity or differences can be determined by a variety of methods, including but not limited to: nucleic acid sequencing, alignment of sequencing reads, gel electrophoresis, restriction enzyme digests, single strand conformational polymorphism, and so on.

The terms "detecting" and "detection" are used in a broad sense herein and encompass any technique by which one can determine the presence of or identify a nucleic acid sequence. In some embodiments, detecting comprises quantitating a detectable signal from the nucleic acid, including without limitation, a real-time detection method, such as quantitative PCR ("Q-PCR"). In some embodiments, detecting comprises determining the sequence of a sequencing product or a family of sequencing products generated using an amplification product as the template; in some embodiments, such detecting comprises obtaining the sequence of a family of sequencing products. In other embodiments detecting can be achieved through measuring the size of a nucleic acid amplification product.

As used herein, "DNA" refers to deoxyribonucleic acid in its various forms as understood in the art, such as genomic DNA, cDNA, isolated nucleic acid molecules, vector DNA, and chromosomal DNA. "Nucleic acid" refers to DNA or RNA in any form. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA molecules. Typically, an "isolated" nucleic acid is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, is generally substantially free of other cellular material or culture medium when produced by recombinant techniques, or free of chemical precursors or other chemicals when chemically synthesized.

As used herein, the term "flanking sequence" broadly refers to nucleic acid sequence 5' and/or 3' of a target nucleic acid sequence, including, but not limited to, a short tandem repeat sequence. The flanking sequence can be within an amplification product or outside, i.e., flanking, the amplification product. Amplification primers can be selected to hybridize to sequences flanking the variable portion of an STR marker so as to produce amplicons of a size indicative of a specific allele of the STR marker As used herein, the term "short tandem repeat (STR) loci" refers to regions of a genome which contains short, repetitive sequence elements of 2 to 7 base pairs in length. Each sequence element is repeated at least once within an STR and is referred to herein as a "repeat unit." The term STR also encompasses a region of genomic DNA wherein more than a single repeat unit is repeated in tandem or with intervening bases, provided that at least one of the sequences is repeated at least two times in tandem. Examples of STRs, include but are not limited to, a triplet repeat, e.g., ATC in tandem, e.g., ATCATCATCATCAACATCATC (SEQ ID NO:1); a 4-peat (tetra-repeat), e.g., GATA in tandem, e.g., GATAGATAGATACATAGATA (SEQ ID NO:2); and a 5-peat (pentarepeat), e.g., ATTGC in tandem, e.g., ATTGCATTGCATTGC (SEQ ID NO:3) and so on. Information about specific STRs that can be used as genetic markers can be found in, among other places, the STRbase at www.cstl.nist.gov/strbase.

As used herein, the terms "imperfect repeat", "incomplete repeat", and "variant repeat" refer to a tandem repeat within which the repeat unit, though in tandem, has sequence interruptions (additions or deletions) between one or more repeat units, e.g., ATCG ATCG AACG ATCG ATCG (SEQ ID NO:4), where the third repeat unit is not identical to the other repeat units and so an imperfect repeat; an incomplete repeat can be seen as a tandem repeat in which the number of base pairs in a repeat unit is an incomplete repeat, e.g., allele 9 of the TH01 locus contains nine 4-peat repeat units ([AATG]$_9$ (SEQ ID NO: 8) for the complete repeat "AATG" for the TH01 locus, but the 9.3 allele contains the nine "AATG" repeats and one incomplete repeat, "ATG" of three nucleotides, an incomplete repeat, i.e., [AATG]$_6$ATG[AATG]$_3$ (SEQ ID NO: 9); while a variant repeat has variation(s) within the repeat unit, e.g., ATCC ATCG ATCC ATCG ATCG ATCC ATCC (SEQ ID NO:5), where the 4-peat repeat unit has a variant base pair at the fourth position of the repeat unit, either a "C" or a "G" nucleotide.

As used herein, the term "polymorphic short tandem repeat loci" refers to STR loci in which the number of repetitive sequence elements (and net length of the sequence) in a particular region of genomic DNA varies from allele to allele, and from individual to individual.

As used herein, the term "tandem repeat" refers to a repetitive sequence occurring in sequential succession.

As used herein, the term "tandem repeat locus" refers to a locus containing tandem repeats.

As used herein, "D10S1248, allele-7" refers to the STR marker D10S1248 located at the D10S1248 locus on chromosome 10, at 10q26.3. The allele-7 repeat structure is presumed to be [GGAA]$_7$ (SEQ ID NO: 10) but it is also possible to have variable and imperfect repeats with allele-7. When reference is made to D10S1248, allele-7, envisioned too are possible incomplete, variable and imperfect repeats of D10S1248, allele-7.

As used herein, "D12S391, allele-13" refers to the STR marker D12S391 located at the D12S391 locus on chromosome 12. The allele-13 repeat structure is presumed to be [AGAT]$_6$[AGAC]$_6$[AGAT] (SEQ ID NO: 11). When reference is made to D12S391, allele-13, envisioned too are possible incomplete, variable and imperfect repeats of D12S391, allele-13 is prevalent among other alleles within this marker, e.g., alleles 17 and 17.3, 19 and 19.3, 20 and 20', 21 and 21', 22 and 22', 23 and 23', 24, 24' and 24", 25 and 25', 26 and 26'.

As used herein, "amplify" refers to the process of enzymatically increasing the amount of a specific nucleotide sequence. This amplification is not limited to but is generally accomplished by PCR. As used herein, "denaturation" refers to the separation of two complementary nucleotide strands from an annealed state. Denaturation can be induced by a number of factors, such as, for example, ionic strength of the buffer, temperature, or chemicals that disrupt base pairing interactions. As used herein, "annealing" refers to the specific interaction between strands of nucleotides wherein the strands bind to one another substantially based on complementarity between the strands as determined by Watson-Crick base pairing. It is not necessary that complementarity be 100% for annealing to occur. As used herein, "extension" refers to the amplification cycle after the primer oligonucleotide and target nucleic acid have annealed to one another, wherein the polymerase enzyme catalyzes primer extension, thereby enabling amplification, using the target nucleic acid as a replication template.

The terms "amplicon," "amplification product" and "amplified sequence" are used interchangeably herein and refer to a broad range of techniques for increasing polynucleotide sequences, either linearly or exponentially and can be the product of an amplification reaction. An amplicon can be double-stranded or single-stranded, and can include the separated component strands obtained by denaturing a double-stranded amplification product. In certain embodiments, the amplicon of one amplification cycle can serve as a template in a subsequent amplification cycle. Exemplary amplification techniques include, but are not limited to, PCR or any other method employing a primer extension step. Other nonlimiting examples of amplification include, but are not limited to, ligase detection reaction (LDR) and ligase chain reaction (LCR). Amplification methods can comprise thermal-cycling or can be performed isothermally. In various embodiments, the term "amplification product" and "amplified sequence" includes products from any number of cycles of amplification reactions.

"Genetic markers" are generally alleles of genomic DNA loci with characteristics of interest for analysis, such as DNA typing, in which individuals are differentiated based on variations in their DNA. Most DNA typing methods are designed to detect and analyze differences in the length and/or sequence of one or more regions of DNA markers known to appear in at least two different forms, or alleles, in a population. Such variation is referred to as "polymorphism," and any region of DNA in which such a variation occurs is referred to as a "polymorphic locus." One possible method of performing DNA typing involves the joining of PCR amplification technology (K B Mullis, U.S. Pat. No. 4,683,202) with the analysis of length variation polymorphisms. PCR traditionally could only be used to amplify relatively small DNA segments reliably; i.e., only amplifying DNA segments under 3,000 bases in length (M. Ponce and L. Micol (1992), NAR 20(3):623; R. Decorte et al. (1990), DNA CELL BIOL. 9(6): 461 469). Short tandem repeats (STRs), minisatellites and variable number of tandem repeats (VNTRs) are some examples of length variation polymorphisms. DNA segments containing minisatellites or VNTRs are generally too long to be amplified reliably by PCR. By contrast STRs, containing repeat units of approximately three to seven nucleotides, are short enough to be useful as genetic markers in PCR applications, because amplification protocols can be designed to produce smaller products than are possible from the other variable length regions of DNA.

As used herein, the terms "polynucleotide", "oligonucleotide", and "nucleic acid" are used interchangeably herein and refer to single-stranded and double-stranded polymers of nucleotide monomers, including without limitation 2'-deoxyribonucleotides (DNA) and ribonucleotides (RNA) linked by internucleotide phosphodiester bond linkages, or internucleotide analogs, and associated counter ions, e.g., H$^+$, NH$_4^+$, trialkylammonium, Mg$^{2+}$, Na$^+$, and the like. A polynucleotide may be composed entirely of deoxyribonucleotides, entirely of ribonucleotides, or chimeric mixtures thereof and can include nucleotide analogs. The nucleotide monomer units may comprise any nucleotide or nucleotide analog. Polynucleotides typically range in size from a few monomeric units, e.g. 5-40 when they are sometimes referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine, "G" denotes deoxyguanosine, "T" denotes thymidine, and "U" denotes deoxyuridine, unless otherwise noted.

As used herein, the terms "target polynucleotide," "nucleic acid target" and "target nucleic acid" are used interchangeably herein and refer to a particular nucleic acid sequence of interest. The "target" can be a polynucleotide sequence that is sought to be amplified and can exist in the presence of other nucleic acid molecules or within a larger nucleic acid molecule. The target polynucleotide can be obtained from any source, and can comprise any number of different compositional components. For example, the target can be nucleic acid (e.g. DNA or RNA). The target can be methylated, non-methylated, or both. Further, it will be appreciated that "target polynucleotide" can refer to the target polynucleotide itself, as well as surrogates thereof, for example amplification products, and native sequences. In some embodiments, the target polynucleotide is a short DNA molecule derived from a degraded source, such as can be found in, for example, but not limited to, forensics samples (see for example Butler, 2001, Forensic DNA Typing: Biology and Technology Behind STR Markers). The target polynucleotides of the present teachings can be derived from any of a number of sources. These sources may include, but are not limited to, whole blood, a tissue biopsy, lymph, bone, bone marrow, tooth, amniotic fluid, hair, skin, semen, anal secretions, vaginal secretions, perspiration, saliva, buccal swabs, various environmental samples (for example, agricultural, water, and soil), research samples generally, purified samples generally, and lysed cells. It will be appreciated that target polynucleotides can be isolated from samples using any of a variety of procedures known in the art, for example the PrepSEQ™ Kits (from Applied Biosystems), Boom et al., and U.S. Pat. No. 5,234, 809, etc. It will be appreciated that target polynucleotides can be cut or sheared prior to analysis, including the use of such procedures as mechanical force, sonication, restriction endonuclease cleavage, or any method known in the art.

As used herein, the "polymerase chain reaction" or PCR is a an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., eds, The Polymerase Chain Reaction, BirkHauser, Boston, Mass. (1994)). Each of the above steps may be conducted at a different temperature, preferably using an automated thermocycler (Applied Biosystems LLC, a division of Life Technologies Corporation, Foster City, Calif.). If desired, RNA samples can be converted to DNA/RNA heteroduplexes or to duplex cDNA by methods known to one of skill in the art. The PCR method also includes reverse transcriptase-PCR and other reactions that follow principles of PCR.

The term "primer" refers to a polynucleotide (oligonucleotide) and analogs thereof that are capable of selectively hybridizing to a target nucleic acid or "template", a target region flanking sequence or to a corresponding primer-binding site of an amplification product; and allows the synthesis of a sequence complementary to the corresponding polynucleotide template, flanking sequence or amplification product from the primer's 3' end. Typically a primer can be between about 10 to 100 nucleotides in length and can provide a point of initiation for template-directed synthesis of a polynucleotide complementary to the template, which can take place in the presence of appropriate enzyme(s), cofactors, substrates such as nucleotides (dNTPs) and the like.

As used herein, the terms "amplification primer" and "oligonucleotide primer" are used interchangeably and refer to an oligonucleotide, capable of annealing to an RNA or DNA region adjacent a target sequence, and serving as an initiation primer for DNA synthesis under suitable conditions well known in the art. Typically, a PCR reaction employs an "amplification primer pair" also referred to as an "oligonucleotide primer pair" including an "upstream" or "forward" primer and a "downstream" or "reverse" primer, which delimit a region of the RNA or DNA to be amplified. A first primer and a second primer may be either a forward or reverse primer and are used interchangeably herein and are not to be limiting.

As used herein, the term "primer-binding site" refers to a region of a polynucleotide sequence, typically a sequence flanking a target region and/or an amplicon that can serve directly, or by virtue of its complement, as the template upon which a primer can anneal for any suitable primer extension reaction known in the art, for example, but not limited to, PCR. It will be appreciated by those of skill in the art that when two primer-binding sites are present on a double-stranded polynucleotide, the orientation of the two primer-binding sites is generally different. For example, one primer of a primer pair is complementary to and can hybridize with the first primer-binding site, while the corresponding primer of the primer pair is designed to hybridize with the complement of the second primer-binding site. Stated another way, in some embodiments the first primer-binding site can be in a sense orientation, and the second primer-binding site can be in an antisense orientation. A primer-binding site of an amplicon may, but need not comprise the same sequence as or at least some of the sequence of the target flanking sequence or its complement.

Those in the art understand that as a target region is amplified by certain amplification means, the complement of the primer-binding site is synthesized in the complementary amplicon or the complementary strand of the amplicon. Thus, it is to be understood that the complement of a primer-binding site is expressly included within the intended meaning of the term primer-binding site, as used herein.

As used herein, the term "mobility modifier" refers to a non-nucleotide linker between a dye attached to the 5' end of a PCR primer and the PCR primer's 5' end. Examples of mobility modifiers include, but are not limited to, oligo ethylene oxide mobility modifiers such as hexaethyleneoxide (HEO) (Grossman et al. NAR 22:2527-2534 (1994)), U.S. Pat. Nos. 5,470,705; 5,703,222 and 5,989,871, incorporated by reference herein.

As used herein, the term "nucleic acid sample" refers to nucleic acid found in biological samples according to the present invention including, but not limited to, for example, hair, feces, blood, tissue, urine, saliva, cheek cells, vaginal cells, skin, for example skin cells contained in fingerprints, bone, tooth, buccal sample, amniotic fluid containing placental cells, and amniotic fluid containing fetal cells and semen. It is contemplated that samples may be collected invasively or noninvasively. The sample can be on, in, within, from or found in conjunction with a fiber, fabric, cigarette, chewing gum, adhesive material, soil or inanimate objects. "Sample" as used herein, is used in its broadest sense and refers to a sample suspected of containing a nucleic acid and can comprise a cell, chromosomes isolated from a cell (e.g., a spread of metaphase chromosomes), genomic DNA, RNA, cDNA and the like. Samples can be of animal or vegetable origins encompassing any organism containing nucleic acid, including, but not limited to, bacteria, viruses, plants, livestock, household pets, and human samples.

Also herein, the recitations of numerical ranges by endpoints include all numbers subsumed within that range (e.g., 1 to 5 includes 1, 1.5, 2, 2.75, 3, 3.80, 4, 5, etc.).

Various embodiments of the present teachings relate to newly discovered alleles of STRs D10S1248 and D12S391. Embodiments of the claimed inventions include allelic ladders for the detection of these novel alleles of D10S1248 and D12S391. In some embodiments, the allelic ladder for each locus has in combination, an isolated plurality of nucleic acid molecules that serve as size standards for allele 7 of the D10S1248 marker or the allele 13 of the D12S391 marker. An allele within a locus comprises a nucleic acid molecule having a polymorphic tandemly repeated base pair motif. It is the variation in the number of repeat units in tandem that distinguish alleles within a locus.

The terms for the particular STR loci as used herein refer to the names assigned to these loci as they are known in the art. The loci are identified, for example, in the various references and by the various accession numbers in the list that follows, all of which are incorporated herein by reference in their entirety. The list of references that follows is merely intended to be exemplary of sources of locus information. The information regarding the DNA regions comprising these loci and contemplated for allelic ladder construction are publicly available and easily found by consulting the following or other references and/or accession numbers. Where appropriate, the current Accession Number as of time of filing is presented, as provided by GenBank® (National Center for Biotechnology Information, Bethesda, Md.). See, e.g., for the locus D10S1248, M D Coble and J M Butler (2005), J. FORENSIC Sci. 50(1):43-53, GenBank Accession No. AL391869; and for D12S391, M V Lareu et al. (1996), GENE 182:151-153, GenBank Accession No. G08921.

Heretofore, the D10S1248 marker, located on the long arm of chromosome 10 at position 10q26.3, was reported to consist of 12 alleles with tandem repeats of the "GGAA" tetra-repeat ranging from 8 tandem repeats to 19 tandem repeats (SEQ ID NO: 12) (NIST Standard Reference Database SRD 130, Gaithersburg, Md.). The present teachings encompass a newly discovered allele-7 presumed to have 7 "GGAA" tandem repeats (SEQ ID NO: 10). In all reported cases, the D10S1248 tandem repeats are perfect repeats. That is, the "GGAA" repeat appears seven times in tandem for allele-7 (SEQ ID NO: 10), eight times in tandem for allele-8 (SEQ ID NO: 13) and so on.

The D12S391 marker, located on chromosome 12, was previously reported to have 15 alleles and an additional 8 microvariant alleles represented as a compound repeat; [AGAT]$_{8-17}$[AGAC]$_{6,8-10}$[AGAT]$_{0-1}$ (SEQ ID NO: 14) (NIST, supra). The reported tandem repeats ranged from 15 repeats to 26 repeats. The present teachings provide three new alleles for D12S391, new alleles -13, -14 and -27 having 13, 14 and 27 tandem repeats, respectively.

The new alleles for each locus can be summarized by Table 1:

TABLE 1

| Locus | New Allele | Amplicon size range for ladder | Size of the STR repeat (bp) |
|---|---|---|---|
| D10S1248 | 7 | 78-122 bp | 28 |
| D12S391 | 13 | 203 bp | 52 |
| | 14 | 207 bp | 56 |
| | 27 | 259 bp | 108 |

The alleles within the newly developed allelic ladders are summarized in Table 2. The number of alleles represented in Table 2 do not distinguish the alleleic repeats as being perfect, imperfect, variable or incomplete, as any combination of allele types are envisioned for composing an allelic ladder.

TABLE 2

| Locus | No. of alleles in allelic ladder | Allelic ladder range | Amplicon size range for ladder | Size of the STR repeat for first allele (bp) |
|---|---|---|---|---|
| D10S1248 | 12 | 7-18 | 78-122 bp | 28 |
| | 13 | 7-19 | 78-126 bp | |
| D12S391 | 15* | 13-27 | 203-259 bp | 52 |

The D10S1248 allele-7 and alleles -13, -14, and -27 for D12S391 were identified in samples IBB-83, IBB-725, IBB-923 and IBB-496, respectively (Interstate Blood Bank, Inc., Memphis, Tenn.) during a multiplex screen of 624 population samples of human genomic DNA.

The electropherogram for IBB-83 indicated heterozygocity for the D10S1248 marker. The two peaks represented new allele-7 falling outside of the "tracking ladder" and a peak at allele-14. The allelic ladder used to identify allele-7 for D10S1248 contained 11 size standards, representing alleles 8-18.

The electropherogram for IBB-725 indicated that the individual was a heterozygote for the D12S391 marker. Two peaks were observed, one represented new allele-13 and fell outside of the "tracking ladder" and a second peak for allele-15. The electropherogram for IBB-923 indicated that the individual was a heterozygote for the D12S391 marker. Two peaks were observed, one represented new allele-14 and a second peak for allele-18. The electropherogram for IBB-496 indicated that the individual was a heterozygote for the D12S391 marker. Two peaks were observed, one represented allele-23 and the second peak was that of new allele-27. The allelic ladder used to identify alleles -13, -14, and -27 for D12S391 contained 12 size standards, representing alleles 15-26.

In some embodiments, the allelic ladder is a mixture of at least one of the D10S1248 allelic ladder and the D12S391 allelic ladder. In other embodiments, the allelic ladder is a mixture of at least the D10S1248 allelic ladder and the D12S391 allelic ladder. In yet other embodiments, the allelic ladder is a mixture of the D10S1248 allelic ladder and the D12S391 allelic ladder and includes the newly identified alleles disclosed herein as shown in Table 1. The D10S1248 ladder includes alleles ranging from 78 base pairs (allele-7) to 122 base pairs (allele-18) and the D12S391 allelic ladder includes alleles ranging from 203 base pairs (allele-13) to 263 base pairs (allele-27). The sequences of D12S391 allele-14 and allele-27 were cloned into a plasmid vector and sequenced. FIG. 1 shows the sequence data for alleles -14 and -27.

One embodiment of an allelic ladder was constructed by identifying individuals within the Applied Biosystems inhouse DNA collection which possess alleles that are representative of the STR variations for the particular STR marker. The Applied Biosystems DNA collection consists of 1251 DNA samples (395 Hispanic, 350 Caucasian, 350 African American and 156 Asians). The DNAs were previously genotyped with other commercially available STR multiplex kits such as the AmpF/STR® Identifiler® kit (Applied Biosystems, Foster City, Calif.). The alleles for each locus are first amplified by PCR and then cloned into bacteria using a TOPO® TA approach (Invitrogen, Carlsbad, Calif.). DNA sequencing for a small number of clones for each of the newly identified alleles can be performed to ascertain that the correct allele was cloned. Results of the sequencing of D12S391 allele-14 and allele-27 are shown in FIG. 1.

In some embodiments, the present teachings relate to methods for detecting and identifying alleles of a short tandem (STR) repeat sequence in a target nucleic acid. In some embodiments, the method for detecting and identifying alleles of a STR sequence includes amplifying at least one short tandem repeat sequence from a target nucleic acid by polymerase chain reaction (PCR) using locus-specific oligonucleotide primers. The same locus-specific oligonucleotide primers are used for both the sample and the allelic ladder for the marker and the primers are specific to either the D10S1248 or D12S391 marker. The STR sequence is located within the short tandem repeat locus of either D10S1248 or D12S391. Following amplification, the amplification product's resulting amplified short tandem repeat sequence is compared with the amplified allelic ladder to call the allele based on matching the sample's amplification product to the allele standard found within the allelic ladder. In some embodiments, the method for detecting and identifying alleles of a short tandem repeat sequence uses PCR amplification of the target nucleic acid and employs oligonucleotide primer pairs. PCR primer pairs for D10S1248 and D12S391 are readily available from STRbase or can be designed by methods routine to one of skill in the art.

In some embodiments the electrophoretic mobility of the amplification product, i.e., amplicon containing the STR for a given locus, can be adjusted to avoid overlapping with the electrophoretic mobility range of another, different STR locus amplicon. This can be done in at least two different approaches that may be used in isolation or in combination with one another. In one approach, the position of the primers is adjusted to create either a smaller or larger amplification product to avoid overlapping the molecular weight size of another locus during electrophoresis. In another approach, mobility modifiers including, but not limited to, for example, hexaethyleneoxide (HEO), as a non-nucleotide linker between the fluorescent dye at the 5'-end of the primer and the primer sequence can be employed. See, for example, U.S. Pat. Nos. 6,395,486 and 6,734,296, incorporated herein by reference, in their entirety. Similarly, the amplification primers may contain additional nucleotides (at the 5' end) that do not hybridize to the locus, but are added to create the desired mobility of the amplicon for the detection method employed, e.g., electrophoresis or mass spectroscopy. The resulting PCR amplification product (of the larger of the two PCR products) contains the mobility modifier molecules, increasing the molecular weight of the PCR product and thus a perceived shift in the molecular weight of the larger PCR product to an even larger size.

Methods for analyzing nucleic acids are well known to one of skill in the art as are methods for amplification by PCR. The analyses of the PCR amplification product, i.e., amplicon, includes, but is not limited to, detection, identification and in some instances, sequencing the amplification product, methods well established and known to one of skill in the art. In some embodiments, the method for detecting and identifying alleles of a short tandem repeat sequence involves comparing the amplified short tandem repeat amplification sequence to the corresponding allelic ladder by electrophoresis. Many electrophoresis methods for the separation of alleles are known to one of skill in the art and include, but are not limited to, denaturing and non-denaturing gel electrophoresis, capillary electrophoresis, and the like. In some embodiments, the subject allelic ladders provide the advantage of being available to run simultaneously with the amplified short tandem repeat amplification sequence during electrophoresis and comparing banding patterns of the allelic ladder and the amplified sample. Methods for sequencing the amplification product, e.g., Sanger sequencing are well established and known to one of skill in the art.

In some embodiments of the present teachings, methods are provided wherein one or more samples are analyzed for the determination of STR alleles present in the sample. In some embodiments, the samples are tested to see if they contain allele-7 of D10S1248 or allele-13 of D12S391. In some embodiments, the method includes isolating nucleic acid from the sample and PCR amplifying the nucleic acid to generate an amplification product. The amplification product is then compared to an allelic ladder mixture comprising one or more allelic ladders. The allelic ladders selected for locus D10S1248 can have alleles -7 to -18 or alleles -7 to -19. The allelic ladder for locus D12S391 can have alleles -13 to -27.

In some embodiments, the sample comprising the target nucleic acid being analyzed is from one or more of hair, feces, blood, tissue, urine, saliva, cheek cells, vaginal cells, skin, bone, tooth, buccal sample, amniotic fluid containing placental cells, and amniotic fluid containing fetal cells and semen. In some embodiments, the sample may originate from a crime scene, a sample associated with a crime scene, a sample taken from a suspect, a reference sample or a sample taken from a human under consideration. In other embodiments, the sample may be an archeological sample, a maternity sample, a paternity sample, a missing person sample.

In some embodiments, the present teachings are directed to kits for analyzing a short tandem repeat sequence from a nucleic acid sample that utilize the methods described above. In some embodiments, a kit for analyzing a short tandem repeat sequence in a nucleic acid sample includes at least one receptacle containing an allelic ladder selected from the group consisting of the D10S1248 allelic ladder that includes allele-7 and the D12S391 allelic ladder that includes allele-13. In some embodiments, a basic kit can have at least one allelic ladder. The allelic ladder can be directed to D10S1248 or D12S391 or the allelic ladder can comprise an allelic ladder mixture of at least D10S1248 and D12S391 allelic ladders. The kit can also have other optional kit components, such as, for example, one or more of the following components: an oligonucleotide primer pair capable of amplifying marker D10S1248 so as to produce amplicons of a size corresponding to at east one individual size standard in the allelic ladder included in the kit, and a target nucleic acid sample, an oligonucleotide primer pair capable of amplifying marker D10S1248 so as to produce amplicons of a size corresponding to at least one individual size standard in the allelic ladder included in the kit, marker D12S391 and a target nucleic acid sample, a sufficient quantity of enzyme for amplification, amplification buffer to facilitate the amplification, a divalent cation solution to facilitate enzyme activity, dNTPs for strand extension during amplification, loading solution for preparation of the amplified material for electrophoresis, genomic DNA as a template control, a size marker to insure that materials migrate as anticipated in the separation medium, and a protocol and manual to educate the user and limit error in use. The amounts of the various reagents in the kits also can be varied depending upon a number of factors, such as the optimum sensitivity of the process. It is within the scope of these teachings to provide test kits for use in manual applications or test kits for use with automated sample preparation, reaction set-up, detectors or analyzers.

Those in the art understand that the detection techniques employed are generally not limiting. Rather, a wide variety of detection means are within the scope of the disclosed methods and kits, provided that they allow the presence or absence of an amplicon to be determined.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

Aspects of the present teachings may be further understood in light of the following examples, which should not be construed as limiting the scope of the present teachings in any way.

EXAMPLES

Those having ordinary skill in the art will understand that many modifications, alternatives, and equivalents are possible. All such modifications, alternatives, and equivalents are intended to be encompassed herein.

The following procedures are representative of reagents and procedures that can be employed for the isolation and amplification of a target nucleic acid in a sample and the detection, identification and analysis of short tandem repeat sequences in polymorphic loci D10S1248 and D12S391 and the allelic ladders made therefrom.

Sample Amplification

Example A

Construction of an Allelic Ladder

Blood samples from individuals identified to have alleles that are representative of the variations for the particular STR marker are collected and DNA is isolated from the blood samples by methods known to one of skill in the art. DNA is amplified for the alleles of interest with PCR primers for the locus of interest.

1. Prepare a 25 μl PCR Reaction:

| | |
|---|---|
| DNA Template (>1 ng) | 10.0 μl |
| 10X PCR Buffer | 2.5 μl |
| 25 mM MgCl$_2$ | 2.0 μl |
| 50 mM dNTPs (0.2 mM of each nucleotide) triphosphate (dATP, dCTP, dGTP, dTTP)) | 0.10 μl each dNTP |
| Primers (100-200 ng each) 1 μM each | 0.75 μl |
| AmpliTaq Gold ® DNA Polymerase (1 unit/μl) | 1.25 μl |
| Water | 8.4 μl |

Use less DNA if you are using plasmid DNA as a template and more DNA if you are using genomic DNA as a template.

Thermalcycling conditions:

94° C./11 min→30 cycles [94° C./15 sec, 60° C./30 sec, 72° C./45 sec]→72° C./30 min→4° C./hold. A 7 to 30 minute extension at 72° C. is included after the last cycle to ensure that all PCR products are full length and 3' adenylated. The PCR product is verified by agarose gel electrophoresis and then cloned into a plasmid using Topo® TA Cloning Reaction Kit (Invitrogen, Carlsbad, Calif.), following the manufacture's directions.

2. Cloning Reaction:

| | Reagent* | |
|---|---|---|
| | Chemically Competent E. coli | Electrocompetent E. coli |
| Fresh PCR product | 0.5 to 4 μl | 0.5 to 4 μl |
| Salt Solution | 1 μl | — |
| Dilute Salt Solution | — | 1 μl |
| Water | add to a total volume of 5 μl | add to a total volume of 5 μl |
| TOPO ® vector | 1 μl | 1 μl |
| Final Volume | 6 μl | 6 μl |

*Store all reagents at −20° C. when finished. Salt solutions and water can be stored at room temperature or +4° C.

The reaction was mixed gently and incubated for 5 minutes at room temperature (22-23° C.). The cloning reaction can be varied from 30 seconds to 30 minutes. For routine subcloning of PCR products, 30 seconds may be sufficient while in the case of large PCR products (>1 kb) or a pool of PCR products an increase the reaction time will yield more colonies. The reaction was placed on ice following incubation or stored at −20° C.

3. Transforming Competent Cells

One Shot® Mach1™T1R chemically competent *E. coli* cells (Invitrogen) were transformed using the cloning reaction for "chemically competent *E. coli*. Selective plates were either ampicillin or kanamycin selective. The later required incubation overnight to visualize colonies.

The vial of S.O.C. medium was warmed to room temperature and the selective plates were warmed to 37° C. for at least 30 minutes. 40 μl of 40 mg/ml X-gal was spread on each LB plate and incubated at 37° C. until used. A single vial of One Shot® cells for each transformation was thawed and held on ice until used.

Method for One Shot® Chemical Transformation was performed following the vendors instructions:

1. To a vial of One Shot® Chemically Competent *E. coli* cells, add 2 μl of the TOPO® Cloning reaction and mix gently, but avoid pipetting up and down to mix and incubate on ice 5 to 30 minutes.
2. Heat-shock the cells for 30 seconds at 42° C. without shaking and immediately transfer to ice.
3. Add 250 μl of room temperature S.O.C. medium.
4. Cap the tube tightly and shake the tube horizontally (200 rpm) at 37° C. for 1 hour.
5. After horizontal shaking, spread 10-50 μl from each transformation on a prewarmed selective plate. Add additional 20 µl of S.O.C. at room temperature can be added to facilitate spreading. Plating two different volumes will assist in having well-spaced colonies on at least one of the two selective plates.

6. Incubate plates at 37° C. For ampicillin selection, visible colonies can appear after 8 hours with and blue/white screening after 12 hours. For kanamycin selection, incubate plates overnight.
7. Pick ~10 white or light blue colonies for analysis, avoiding dark blue colonies.

The selected colonies were either grown in culture overnight when large quantities of DNA were needed and/or used for DNA sequencing in order to ascertain that the correct allele was cloned. High quality DNA for each allele was isolated from the plasmid clone and amplified. The clonal prep was repeated for each allele of a locus. The allele preparations were quantified, with typical concentrations ranging from 50 to 350 ng/uL. The resulting amplified alleles formed the "seeds" for the allelic ladder for each locus.

The synthesis of an allelic ladder for a locus involves an iterative process of PCR amplification of dilutions from the allele seed stocks, comparing the resulting peak heights for each allele, determining an optimum peak height for the ladder and adjusting dilutions in order to ultimately obtain even peak heights for each allele in the ladder. Construction of allelic ladders is known to one of skill in the art and exemplary methods can be found in U.S. Pat. Nos. 5,783,406 and 7,087,380, each incorporated herein by reference for the construction of an allelic ladder.

Thermal Cycle conditions: 95° C./11 min., 32 cycles (94° C./20 sec., 61° C./2 min., 72° C./2 min.), 60° C./75 min., followed by 4° C./hold. Thermalcycling was performed on an Applied Biosytems 9700 thermal cycler (Applied Biosystems, Foster City, Calif.) set to MAX thermal cycling mode with the reaction volume set to 100 uL.

Vendor sources for reagents:
AmpliTaq Gold® DNA Polymerase, 12×250 units with Gold Buffer and MgCl$_2$ solution, (P/N 4311820, Applied Biosystems, Foster City, Calif.)
GeneAmp® dNTP Blend, 100 mM, (N8080261, Applied Biosystems)
Glycogen, from mussel, Roche Diagnostics Corp. (P/N 10901393001)
GenScan™ 600 LIZ™ Size Standard, (P/N 4366589, Applied Biosystems)
Hi-Di™ Formamide, (P/N 4311320, Applied Biosystems)

What is claimed is:

1. An allelic ladder comprising, in combination, an isolated plurality of nucleic acid molecules which are allelic variants of one or more polymorphic short tandem repeat loci, wherein the polymorphic short tandem repeat locus is at least one of D10S1248 comprising allele-7 and D12S391 comprising allele-13, wherein D10S1248 allele-7 is short tandem repeats consisting of the sequence of SEQ ID NO: 10 and wherein D12S391 allele-13 is not an imperfect, incomplete or variant repeat of SEQ ID NO: 11.

2. The allelic ladder of claim 1, wherein the short tandem repeat locus is selected from D10S1248 and D12S391.

3. The allelic ladder of claim 2, wherein the allelic ladder of D10S1248 contains at least 12 alleles and wherein the allelic ladder of D12S391 contains at least 14 alleles.

4. An allelic ladder mixture comprising an allelic ladder for one or more of the following loci, with lowest and highest allele designation as shown, wherein D10S1248 allele-7 is not an imperfect, incomplete or variant repeat of SEQ ID NO: 10 and wherein D12S391 allele-13 is not an imperfect, incomplete or variant repeat of SEQ ID NO: 11:

| Locus | Low MW Allele | High MW Allele |
|---|---|---|
| D10S1248 | 7 | 19 |
| D12S391 | 13 | 27. |

5. The allelic ladder mixture according to claim 4, wherein the mixture includes allelic ladders for loci D10S1248 and D12S391.

6. The allelic ladder mixture according to claim 4, wherein the D10S1248 ladder includes alleles ranging from 78 base pairs upwards and/or from 122 base pairs downward and the D12S391 ladder includes alleles ranging from 203 base pairs upwards and/or from 259 base pairs downward.

7. The allelic ladder mixture according to claim 6, further comprising a mobility modifier.

8. The allelic ladder mixture according to claim 7, wherein the mobility modifier is hexaethyleneoxide (HEO).

9. A method for detecting and identifying alleles of a short tandem repeat sequence comprising:
(a) amplifying at least one short tandem repeat sequence from a target nucleic acid sample by polymerase chain reaction (PCR) using locus-specific oligonucleotide primers, wherein the at least one short tandem repeat sequence is located within a short tandem repeat locus, and
(b) comparing the at least one amplified short tandem repeat sequence to an allelic ladder as recited in claim 1 corresponding to the short tandem repeat locus.

10. The method of claim 9, wherein in step (a) the locus-specific oligonucleotide primers amplify both the allelic ladder and the target nucleic acid sample by polymerase chain reaction.

11. The method of claim 9, wherein in the at least one amplified short tandem repeat sequence is compared to the corresponding amplified allelic ladder by electrophoresis of the amplified short tandem repeat sequence and the amplified allelic ladder and comparing banding patterns of the sample and the allelic ladder.

12. The method according to claim 9, wherein the target nucleic acid sample is from one or more of hair, feces, blood, tissue, urine, saliva, cheek cells, vaginal cells, skin, bone, tooth, buccal sample, amniotic fluid containing placental cells, and amniotic fluid containing fetal cells and semen.

13. The method according to claim 12, wherein the target nucleic acid sample is one or more of a sample obtained from a crime scene, a sample associated with a crime scene, a sample taken from a suspect, a reference sample or a sample taken from a human under consideration.

14. A kit for analyzing a short tandem repeat sequence from a nucleic acid sample, the kit comprising at least one receptacle containing one or more allelic ladders as recited in claim 1.

15. The kit of claim 14, further comprising at least one oligonucleotide primer pair which amplifies the alleles of at least one polymorphic short tandem repeat locus of a nucleic acid sample.

16. The kit of claim 15, wherein at least one oligonucleotide primer comprises a label.

17. The kit according to claim 16, wherein at least one oligonucleotide primer comprises a mobility-modifier.

18. The kit according to claim 17, wherein the mobility-modifier is HEO.

19. The kit according to claim 14, further comprising one or more of a polymerase, a detectable reporter, and a protocol.

20. A kit for analyzing a short tandem repeat sequence from a nucleic acid sample, the kit comprising, an allelic ladder for detecting allele-7 of D10S1248, and a pair of amplification primers for producing an amplification product from the D10S1248 locus and an allelic ladder for detecting allele-13 of D12S391, and a pair of amplification primers for producing an amplification product from the D12S391 locus, wherein D10S1248 allele-7 is short tandem repeats consisting of the sequence of SEQ ID NO: 10 and wherein D12S391 allele-13 is not an imperfect, incomplete or variant repeat of SEQ ID NO: 11.

21. The kit of claim 20, wherein at least one amplification primer comprises a label.

22. The kit according to claim 20, wherein at least one amplification primer comprises a mobility-modifier.

23. The kit according to claim 22, wherein the mobility-modifier is HEO.

24. The kit according to claim 20, further comprising one or more of a polymerase, a detectable reporter, and a protocol.

* * * * *